(12) United States Patent
Kurz

(10) Patent No.: US 6,319,267 B1
(45) Date of Patent: *Nov. 20, 2001

(54) INTRAVASCULAR DEVICE PUSH WIRE DELIVERY SYSTEM

(75) Inventor: Daniel R. Kurz, Sunnyvale, CA (US)

(73) Assignee: Micrus Corporation, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/625,627

(22) Filed: Jul. 25, 2000

Related U.S. Application Data

(63) Continuation of application No. 09/211,835, filed on Dec. 15, 1998, now Pat. No. 6,102,932.

(51) Int. Cl.⁷ .................................................. A61B 17/12
(52) U.S. Cl. .......................................... 606/198; 128/899
(58) Field of Search ............................... 606/1, 198, 200; 128/899

(56) References Cited

U.S. PATENT DOCUMENTS

| | | |
|---|---|---|
| 1,341,052 | 5/1920 | Gale . |
| 1,667,730 | 5/1928 | Green . |
| 2,078,182 | 4/1937 | MacFarland . |
| 2,549,335 | 4/1951 | Rahthus . |
| 3,334,629 | 8/1967 | Cohn . |

(List continued on next page.)

FOREIGN PATENT DOCUMENTS

| | | |
|---|---|---|
| 4102550 A1 | 8/1991 | (DE) . |
| 0 183372 A1 | 6/1986 | (EP) . |
| 0 358 767 A1 | 3/1990 | (EP) . |
| 0 382014 A1 | 8/1990 | (EP) . |
| 0 941 700 A1 | 9/1999 | (EP) . |
| 592.182 | 7/1925 | (FR) . |
| 2 066 839 A | 7/1981 | (GB) . |
| WO 97/01368 | 1/1997 | (WO) . |
| WO 98/02100 | 1/1998 | (WO) . |
| WO 99/32037 | 7/1999 | (WO) . |

OTHER PUBLICATIONS

International Search Report Dated May 3, 2001.
Retrievable Gianturco–Coil Introducer, By Jeffrey Hawkins, Ronald G. Quisling, MD, J. Parker Mickle, MD an Irvin F. Hawkins, MD (Radiology 1986) From the Depts. Of Radiology and Neurosurgery, University of Florida Medical Center and Hawk Prototype Equipment, Gainesville, FL.
Christos A. Athanasoulis, M.D. The New England Journal of Medicine, May 15, 1980 "Therapeutic Applications of Angiography" pp. 1117–1125 (1 of 2).
Christos A. Athanasoulis, M.D. The New England Journal of Medicine, May 22, 1980 "Therapeutic Applications of Angiography" pp. 1174–1179 (2 of 2).

(List continued on next page.)

*Primary Examiner*—David O. Reip
*Assistant Examiner*—William W. Lewis
(74) *Attorney, Agent, or Firm*—Fulwider Patton Lee & Utecht, LLP

(57) ABSTRACT

The endoluminal device delivery assembly and method for release and deployment of an endoluminal therapeutic device at a desired location for treatment within the vasculature of a patient utilizes an elongated flexible tubular catheter with a tubular distal tip formed of a yieldable material mounted to the distal end of the catheter for releasably holding the proximal end of the endoluminal device. The endoluminal device can be dislodged from the tubular distal tip by a pusher member or pressurized fluid to expel the endoluminal device through at the desired location for treatment within the vasculature of a patient. A flexible coil can be mounted to the distal end of the elongated pusher member to provide for improved tracking.

3 Claims, 1 Drawing Sheet

U.S. PATENT DOCUMENTS

| | | |
|---|---|---|
| 3,649,224 | 3/1972 | Anderson et al. . |
| 3,868,956 | 3/1975 | Alfidi et al. . |
| 4,327,734 | 5/1982 | White, Jr. . |
| 4,402,319 | 9/1983 | Handa et al. . |
| 4,494,531 | 1/1985 | Gianturco . |
| 4,512,338 | 4/1985 | Balko et al. . |
| 4,545,367 | 10/1985 | Tucci . |
| 4,638,803 | 1/1987 | Rand . |
| 4,655,771 | 4/1987 | Wallsten . |
| 4,718,907 | 1/1988 | Karwoski et al. . |
| 4,732,152 | 3/1988 | Wallsten et al. . |
| 4,748,986 | 6/1988 | Morrison et al. . |
| 4,768,507 | 9/1988 | Fischell et al. . |
| 4,795,458 | 1/1989 | Regan . |
| 4,800,882 | 1/1989 | Gianturco . |
| 4,813,925 | 3/1989 | Anderson, Jr. et al. . |
| 4,820,298 | 4/1989 | Leveen et al. . |
| 4,830,003 | 5/1989 | Wolff et al. . |
| 4,850,960 | 7/1989 | Grayzel . |
| 4,856,516 | 8/1989 | Hillstead . |
| 4,954,126 | 9/1990 | Wallsten . |
| 4,957,479 | 9/1990 | Roemer . |
| 4,957,501 | 9/1990 | Lahille et al. . |
| 4,990,155 | 2/1991 | Wilkoff . |
| 4,994,069 | 2/1991 | Ritchart et al. . |
| 5,002,556 | 3/1991 | Ishida et al. . |
| 5,026,377 | 6/1991 | Burton et al. . |
| 5,041,084 | 8/1991 | DeVries et al. . |
| 5,064,435 | 11/1991 | Porter . |
| 5,071,407 | 12/1991 | Termin et al. . |
| 5,104,404 | 4/1992 | Wolff . |
| 5,108,407 | 4/1992 | Geremia et al. . |
| 5,109,867 | 5/1992 | Twyford, Jr. . |
| 5,122,136 | 6/1992 | Guglielmi et al. . |
| 5,133,731 | 7/1992 | Butler et al. . |
| 5,133,732 | 7/1992 | Wiktor . |
| 5,141,502 | 8/1992 | Macaluso, Jr. . |
| 5,147,370 | 9/1992 | McNamara et al. . |
| 5,151,105 | 9/1992 | Kwan-Gett . |
| 5,160,341 | 11/1992 | Brenneman et al. . |
| 5,176,625 | 1/1993 | Brisson . |
| 5,176,661 | 1/1993 | Evard et al. . |
| 5,183,085 | 2/1993 | Timmermans . |
| 5,186,992 | 2/1993 | Kite, III . |
| 5,203,772 | 4/1993 | Hammerslag et al. . |
| 5,217,484 | 6/1993 | Marks . |
| 5,222,969 | 6/1993 | Gillis . |
| 5,226,911 | 7/1993 | Chee et al. . |
| 5,228,453 | 7/1993 | Sepetka . |
| 5,234,456 | 8/1993 | Silvestrini . |
| 5,250,071 | 10/1993 | Palermo . |
| 5,261,916 | 11/1993 | Engelson . |
| 5,304,194 | 4/1994 | Chee et al. . |
| 5,312,415 | 5/1994 | Palermo . |
| 5,336,205 | 8/1994 | Zenzen et al. . |
| 5,341,818 | 8/1994 | Abrams et al. . |
| 5,342,387 | 8/1994 | Summers . |
| 5,350,397 | 9/1994 | Palermo et al. . |
| 5,354,295 | 10/1994 | Guglielmi et al. . |
| 5,382,259 | 1/1995 | Phelps et al. . |
| 5,441,516 | 8/1995 | Wang et al. . |
| 5,443,478 | 8/1995 | Purdy . |
| 5,514,176 | 5/1996 | Bosley, Jr. . |
| 5,522,836 | 6/1996 | Palermo . |
| 5,549,624 | 8/1996 | Mirigian et al. . |
| 5,562,641 | 10/1996 | Flomenblit et al. . |
| 5,562,698 | 10/1996 | Parker . |
| 5,569,245 | 10/1996 | Guglielmi et al. . |
| 5,578,074 | 11/1996 | Mirigian . |
| 5,582,619 | 12/1996 | Ken . |
| 5,607,445 | 3/1997 | Summers . |
| 5,609,608 | 3/1997 | Benett et al. . |
| 5,624,461 | 4/1997 | Mariant . |
| 5,637,113 | 6/1997 | Tartaglia et al. . |
| 5,639,277 | 6/1997 | Mariant et al. . |
| 5,643,254 | 7/1997 | Scheldrup et al. . |
| 5,645,564 | 7/1997 | Northrup et al. . |
| 5,649,949 | 7/1997 | Wallace et al. . |
| 5,667,522 | 9/1997 | Flomenblit et al. . |
| 5,676,697 | 10/1997 | McDonald . |
| 5,690,643 | 11/1997 | Wijay . |
| 5,690,666 | 11/1997 | Berenstein et al. . |
| 5,690,671 | 11/1997 | McGurk et al. . |
| 5,695,111 | 12/1997 | Nanis et al. . |
| 5,718,711 | 2/1998 | Berenstein et al. . |
| 5,725,546 | 3/1998 | Samson . |
| 5,733,294 | 3/1998 | Forber et al. . |
| 5,746,769 | 5/1998 | Ton et al. . |
| 5,749,894 | 5/1998 | Engelson . |
| 5,800,455 | 9/1998 | Palermo et al. . |
| 5,807,398 | 9/1998 | Shaknovich . |
| 5,814,062 | 9/1998 | Septka et al. . |
| 5,944,733 | 8/1999 | Engelson . |
| 6,102,932 | * 8/2000 | Kurz ..................................... 606/200 |

OTHER PUBLICATIONS

Alex Berenstein, M.D. and Irvin I. Kricheff, M.D. "Catheter and Material Selection for Transarterial Embolization: Technical Considerations" Radiology, Sep. 1979; pp. 631–639.

O.A. Battista, Et Al. Journal of Applied Polymer Science 1967 "Colloidal Macromolecular Phenomena. Part II. Novel Microcrystals of Polymers" pp. 481–498.

Sadek K. Hilal, M.D. Et Al. Journal of Neurological Surgery "Therapeutic Percutaneous Embolization for Extra–Axial Vascular Lesions of the Head, Neck and Spine" Sep., 1975; pp. 275–287.

Stephen L. Kaufman, M.D. Et Al. Investigative Radiology, May–Jun. 1978 "Transcatheter Embolization with Microfibrillar Collagen in Swine"; pp. 200–204.

Ashok J. Kumar, Et Al., Journal of Neuroradiology (1982) "Preoperative Embolization of Hypervascular Head and Neck Neoplasms Using Microfibrillar Collagen", pp. 163–168.

Richard E. Latchaw, M.D. Et Al., Radiology (1979) "Polyvinyl Foam Embolization of Vascular and Neoplastic Lesions of the Head, Neck and Spine" pp. 669–679.

Stewart R. Reuter, M.D. Et Al. American Journal of Radiology, Sep. 1975 "Selective Arterial Embolization for Control of Massive Upper Gastrointestinal Bleeding" pp. 119–126.

Glenn H. Roberson, Et Al., American Journal of Radiology, Oct. 1979 "Therapeutic Embolization of Juvenile Angiofibroma" pp. 657–663.

Sidney Wallace, M.D. Et Al., Cancer, Oct. 1979 "Arterial Occlusion of Pelvic Bone Tumors"; pp. 322–325 & 661–663.

"Mechanical Devices for Arterial Occlusion" by C. Gianturco, M.D., Et Al., Jul. 1975 pp. 428–435.

"Therapeutic Vascular Occlusion Utilizing Steel Coil Technique: Clinical Applications" by Sidney Wallace, Et Al., Am J. Roentgenol (1976); pp. 381–387.

"Transcatheter Intravascular Coil Occlusion of Experimental Arteriovenous Fistulas", by James H. Anderson, Et Al., AM. J. Roentgenol, Nov. 1977, pp. 795–798.

"'Mini' Gianturco Stainless Steel Coils for Transcatheter Vascular Occlusion" by James H. Anderson, Et Al., From the Department of Diagnostic Radiology at the University of Texas System Cancer Center, Aug. 1978, pp. 301–303.

"A New Improved Coil for Tapered–Tip Catheter for Arterial Occlusion" by Vincent P. Chuang, M.D. Et Al., May 1980, pp. 507–509.

* cited by examiner

INTRAVASCULAR DEVICE PUSH WIRE DELIVERY SYSTEM

RELATED APPLICATION

This is a continuation of Ser. No. 09/211,835 filed Dec. 15, 1998, now U.S. Pat. No. 6,102,932.

BACKGROUND OF THE INVENTION

1. Field of the Invention

This invention relates generally to therapeutic placement of interventional medical devices into the vasculature of the human body. More particularly, this invention concerns a placement system using a catheter with a tip formed of yieldable material to grip and thereby releasably capture a portion of an endoluminal device to be dislodged at a desired location within the body by a device for dislodging the endoluminal device from the catheter tip.

2. Description of Related Art

A type of interventional medical device known as an endoluminal coil is used for a wide variety of therapeutic purposes including the treatment of intracranial vascular aneurysms. A vascular aneurysm is often formed as the result of an abnormal dilation of a blood vessel which weakens the arterial wall and allows it to expand into an adjacent body tissue or cavity. Intracranial aneurysms may be treated to prevent rupturing by placing endoluminal coils through the neck of an opening from the vessel into the interior cavity of the aneurysm. After placement, the coils pose a physical barrier, reducing blood flow into the aneurysm and promoting the formation of an embolus in the aneurysm cavity. The embolus formation in the aneurysm cavity further impedes blood flow into the aneurysm and reduces the blood pressure against the aneurysm wall, thus reducing the possibility of a rupture.

One known method for delivering coils into an intracranial aneurysm involves the use of a catheter and a guidewire with a detachable tip shaped in the form of a coil. Such a system is described in U.S. Pat. No. 5, 312, 415, which is incorporated herein by reference. Microcatheters are known, for example, that allow for navigation into cerebral arteries and entry into intracranial aneurysms. The catheter is guided through the vasculature using a guidewire until it reaches the desired location. The tip of the guidewire is then detached and the coils are pushed into the aneurysm until they occlude at least a portion of the interior of the aneurysm. Although generally effective, this technique has limitations on the accuracy for precision placement of embolic coils in intracranial aneurysms. It would be particularly desirable to have a simple delivery system which allows for precise positioning of embolic coils and virtually instantaneous release once the coils are in place.

One approach which provides for greater accuracy of placement involves attaching a coil to the end of the a guidewire and maneuvering the guidewire to place the embolic coil in the desired location and then releasing the coil from the guidewire. Since the physician has control of the guidewire and the coil is firmly attached to the distal end of the pusher, it is possible to achieve a much higher degree of placement accuracy with this approach. However, to implement this approach, the delivery system must include a release mechanism which can be used to easily decouple the coil from the guidewire while inside tiny blood vessels. A variety of release mechanisms have been proposed for this purpose.

In one known technique for deploying an endoluminal device, endoluminal coils may be released through electrolytic dissolution of a connecting segment between the coil and the distal tip of the guidewire. This method typically involves the application of a positive direct current for a predetermined amount of time which results in the dissolution of a stainless steel connector which holds the coil to the guidewire. Although this method has met with considerable success, the procedure has significant disadvantages. Because the use of electrolytic dissolution is slow and unreliable, the delivery of the devices can be very time consuming and therefore very costly. The increased surgery time also creates a higher risk for the patient. In addition, the secondary effects of dissolving a stainless steel wire in the blood could possibly be detrimental to the patient. For these reasons, a simpler, faster, safer and more reliable method of delivering the devices is needed.

Detachable coil assemblies are also known that use a threaded coupling such that the coil is released when the guidewire is rotated. Another conventional technique uses a heat-releasable adhesive bond to separate the coils from the distal end of the catheter. When laser energy is transferred via a fiber optic cable to the connector, the connector is heated, thereby releasing the heat-sensitive adhesive bond between the connector and coil.

One known implant delivery assembly is activated thermally, and includes a coupling portion made of a shape memory material that interlockingly engages the implant when the shape memory material is in one configuration, and releases the implant in another configuration. The implant is detachably coupled to a pusher formed of shape memory material that allows thermal activation of the decoupling mechanism. The coupling portion is constructed with a deformed shape for holding the implant to the pusher, and a pre-set shape that provides release of the implant when the thermal activation is provided. The coupling portion of the pusher is heated by passing an electric current between the pusher and the body of the patient.

Another detachable embolic coil assembly is known that uses interlocking clasps that are used in a surgical instrument for delivering an embolic coil to a selected site within the vasculature of the human body.

Yet another known embolic coil assembly includes a ball that is forced through an aperture in a socket on the distal end of a pusher to release the coil. After a catheter is inserted and navigated through the vessel, and the coil is in place, a plunger is advanced to press the ball and its coil into the target site.

Some conventional vasoocclusive devices are operated by pulling or jerking the catheter tip from an inflatable balloon, thus potentially compromising the position of the implant. One such device provides for an endovascular wire and tip that can be separated from the holding wire mechanically or electrolytically for the formation of thrombus in blood vessels. However, such devices that release the interventional device by mechanically breaking an intermediate section between the catheter tip and balloon can potentially leave broken or jagged ends that could injure the vasculature.

One conventional releasable balloon catheter used to embolize vascular lesions has a tubular portion made of a material such as a hydrophilic polymer located between the catheter and the balloon that can be broken by torsion of the tubular portion. The tubular portion can be melted by heating the tubular portion, or can be dissolved in the blood when heated, and electrodes are provided for heating the tubular portion. Another conventional technique for separating a balloon from a balloon catheter involves the melting and breaking of a connecting member made from polyvinyl alcohol or trans-polyisoprene between the balloon and the catheter body when power is supplied to electrodes provided for heating the connecting member. When the connecting member is heated to temperatures of about 70° C. and slight tension is applied, the balloon can be separated from the main catheter body. However, such devices that release the interventional device by melting or dissolving the intermediate section between the catheter tip and balloon can also potentially release undesirable particles from the connecting member into the bloodstream.

From the above, it can be seen that a variety of approaches to placing embolic devices have been developed, but all of them are limited in some way by the time to release, the dispersion of particles or chemicals, the introduction of electricity, mechanical force on the implant after placement, or some combination of these affects. There is therefore a need for a precise, controlled method of deploying therapeutic interventional devices without compromising the position of the implant, without presenting broken or jagged ends that can potentially injure the vasculature, and without release undesirable particles or materials into the bloodstream.

Recently, a release system for vasoocclusive coils has been developed involving the use of a microgripper made of shape memory material. The shape memory microgrippers is mechanically actuated by the conversion of laser light to heat energy. Another newly developed type of release mechanism using shape memory materials involves a tube of radially recovering shape memory polymer attached to the distal end of an optical fiber pusher. A device such as an endoluminal coil is introduced into the tube and the tube is compressed or crimped around the end of the coil to hold it in place. Once the coil is in the desired location in the vasculature, the tube of shape memory polymer is heated by passing light through the optical fiber pusher to the distal end of the pusher, thereby causing the tube to recover its original diameter and shape. After the tube has recovered its original shape, it is no longer compressed or crimped around the device and the device is free to slip out of the tube.

In another approach, an endoluminal coil delivery system is provided with a mechanical release mechanism for positioning and delivering a coil within a lumen that utilizes a mechanical latch to engage the coil during positioning. The coil is placed at the distal end of delivery system and includes a fitting at the end of coil which is engaged by jaws. The coil is released from the jaws by advancing a release tube over the jaws, which squeezes the jaws, thereby disengaging them from the fitting.

Another endoluminal coil delivery system utilizes an elongated pusher member with a coil implant detachably coupled to a relatively short flexible distal section of the pusher member by a curved coupling portion of the pusher member that can be thermally activated to transform to a preset release configuration. In another coil delivery system, embolic coils are threaded onto a guide wire ahead of a pusher located within a catheter, allowing several coils to be loaded on the guide wire. In another endoluminal coil delivery system, an end of a vasoocclusive coil is open and adapted to receive and engage a conical or cylindrical tip of a pusher core wire. The tip of the pusher wire may be smooth, grooved or in a semi-machined or sanded condition to achieve good adherence of the pusher core wire to the interior of the vasoocclusive coil.

A shape memory metal actuated separation device is also known that can be used for spacecraft. A segmented nut engages a threaded bolt that is to be held and released and is held together by a nut retainer that is movable with respect to the nut and affixed to a shape memory alloy element. The shape memory alloy element is heated by an electrical resistance heater, thereby moving the retainer which causes disengagement.

In one coil shaped intravascular stent formed into a coil spring, to be used to reinforce an arterial wall, the wire forming the stent has axially spaced rollers or bearings to facilitate advancement and withdrawal of the coil spring, with enlarged beads between the rollers to hold the rollers away from one another.

Thus, it can be seen that there is a continued requirement for reliable vascular device and embolic coil release systems. The present invention meets these and other needs.

SUMMARY OF THE INVENTION

Briefly, and in general terms, the present invention provides for an improved system and method for release and deployment of an endoluminal therapeutic device at a desired location for treatment within the vasculature of a patient, utilizing a yieldable material for releasably holding a portion of the endoluminal therapeutic device, to be dislodged from the yieldable material at the desired location for treatment within the vasculature of a patient.

The invention accordingly provides for an endoluminal device delivery assembly for release and deployment of an endoluminal therapeutic device at a desired location for treatment within the vasculature of a patient, comprising an elongated flexible tubular catheter having a distal end, and a tubular distal tip having a proximal end mounted to the distal end of the catheter, an inner lumen, and a distal end with a surface defining a distal opening, and the tubular distal tip being formed of a yieldable material for releasably holding the proximal end of the endoluminal device within the inner lumen of the tubular distal tip. Means are also provided for dislodging the proximal end of the endoluminal device from the inner lumen of the tubular distal tip to expel the proximal end of the endoluminal device through the distal opening of the tubular distal tip at the desired location for treatment within the vasculature of a patient.

In one presently preferred embodiment, the means for dislodging the proximal end of the endoluminal device from the inner lumen of the tubular distal tip comprises an elongated pusher member coaxially disposed within the elongated flexible tubular catheter having proximal and distal ends, with the proximal end of the pusher member extending from the proximal end of the elongated flexible tubular catheter, and the distal end of the pusher member being adapted to contact and dislodge the proximal end of the endoluminal device from the tubular distal tip. In a preferred aspect, the distal end of the elongated flexible tubular catheter has a frustoconical shape, and the distal end of the pusher member has a frustoconical shape.

In one preferred alternate embodiment, a flexible coil is mounted to the distal end of the elongated pusher member. The flexible coil can be formed from a shape memory polymer, a nickel titanium alloy, stainless steel, platinum, or other similar suitable materials.

In another presently preferred embodiment, the tubular distal tip forms a fluid seal about the proximal end of the endoluminal device, and the means for dislodging comprises a syringe connectable to the proximal end of the elongated flexible tubular catheter for supplying pressurized fluid within the elongated flexible tubular catheter to expel the proximal end of the endoluminal device from the tubular distal tip.

In one presently preferred embodiment, the diameter of the distal end of the tubular distal tip is smaller than the proximal end, allowing the proximal end of the endoluminal device to be captured within the inner lumen of the tubular distal tip; and in a preferred aspect, the elongated flexible tubular catheter has a frustoconical distal end, and the distal tip has a corresponding frustoconical shape. The yieldable material forming the tubular distal tip can comprise a shape memory material, such as a shape memory polymer, a nickel titanium alloy, an elastomer such as polyurethane, nylon, polybutyl terephthalate (PBT), polymers available under the trade names PEBAX, Hytrel, Arnitel, Riteflex, or other similar suitable yieldable materials.

The endoluminal therapeutic device has a stem portion with an enlarged proximal end captured within the inner lumen of the tubular distal tip, and is typically an embolic coil, although the endoluminal therapeutic device can also be a stent, intravascular vena cava filter, or similar device to be implanted at a treatment site in the vasculature of a patient.

The invention also provides for a method of delivering an endoluminal therapeutic device into the vasculature of a patient, comprising the steps of providing an elongated flexible tubular catheter having a tubular distal tip mounted to the distal end of the catheter, the tubular distal tip having an inner lumen and a distal end with a surface defining a distal opening, and the tubular distal tip being formed of a yieldable material for releasably holding the proximal end of the endoluminal device within the inner lumen of the tubular distal tip; and introducing a dislodging element into the proximal end of the elongated flexible catheter to dislodge the proximal end of the endoluminal device from the tubular distal tip to expel the proximal end of the endoluminal device through the distal opening of the tubular distal tip at the desired location for treatment within the vasculature of a patient. In one presently preferred embodiment, the step of introducing a dislodging element comprises introducing an elongated pusher member coaxially within the elongated flexible tubular catheter to contact and dislodge the proximal end of the endoluminal device from the tubular distal tip. Alternatively, when the distal tip forms a fluid seal about the proximal end of the endoluminal device, and the step of introducing a dislodging element can comprise connecting a syringe to the proximal end of the elongated flexible tubular catheter for supplying pressurized fluid within the elongated flexible tubular catheter to expel the proximal end of the endoluminal device from the tubular distal tip.

These and other aspects and advantages of the invention will become apparent from the following detailed description and the accompanying drawings, which illustrate by way of example the features of the invention.

DETAILED DESCRIPTION OF THE PREFERRED EMBODIMENTS

As very small medical instruments such as microcatheters have become available, physicians are now able to reach areas within the human body which were previously inaccessible. Among the areas which can now be accessed in a minimally invasive procedure are the tiny blood vessels within the brain. Using very small diameter pushers, it is now possible to insert therapeutic devices through microcatheters to treat damaged vasculature within the brain such as intracranial aneurysms. However, because the pushers and catheters used to deliver these devices are so small, there are practical limitations associated with their use. For example, because of the size and delicacy of the devices, it is not practical to have a device with complex moving parts at the distal end of the pusher, even though it is important to be able to reliably release the device from the pusher into the vasculature. While various methods for delivery of endoluminal devices to a treatment site within the vasculature have been developed, there remains a need for a reliable method of delivering and placing such devices, particularly into smaller, previously inaccessible areas of the vasculature.

Figure 1:
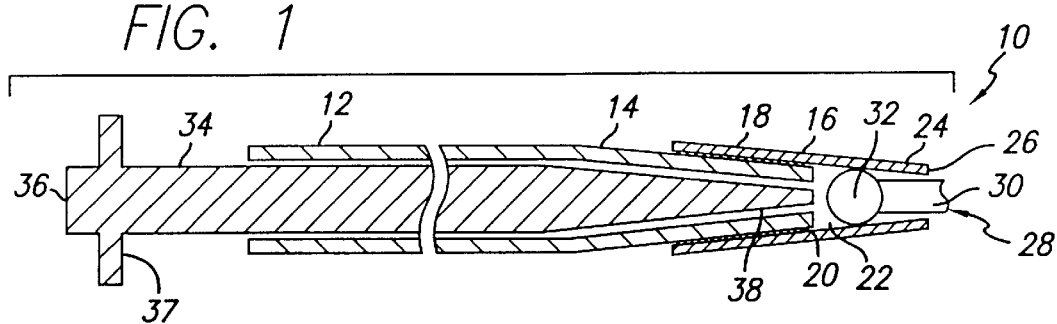
FIG. 1 is a cross-sectional view of a first embodiment of the endoluminal device delivery assembly of the invention.

As is illustrated in the drawings, which are provided by way of example and not by way of limitation, the invention is embodied in an assembly and method for release and deployment of an endoluminal therapeutic device at a desired location for treatment within the vasculature of a patient. Referring to FIG. 1, the endoluminal device delivery assembly 10 includes an elongated flexible tubular catheter 12 having a distal end 14. The catheter can be formed, for example, from polyethylene, polyethylene terephthalate, polyvinyl chloride, nylon and ionomers, or other similar suitable polymers, stainless steel or nickel titanium alloy hypo tubes, and the like. In a preferred embodiment, the distal end of the elongated flexible tubular catheter preferably has a frustoconical shape. The catheter advantageously includes a tubular distal tip 16 having a proximal end 18 mounted to the outer surface of the distal end of the catheter, such as by adhesive bonding, such as with a cyanoacrylate adhesive 20, for example. The tubular distal tip may alternatively be heat bonded to the distal end of the catheter, or may be mounted to the distal end of the catheter by other suitable means. The tubular distal tip has an inner lumen 22, and a distal end 24 with a surface defining a distal opening 26. In one presently preferred embodiment, the diameter of the distal end of the tubular distal tip is smaller than the proximal end, allowing the proximal end of the endoluminal device to be captured within the inner lumen of the tubular distal tip. The elongated flexible tubular catheter preferably has a frustoconical distal end, and the distal tip has a corresponding frustoconical shape. Alternatively, a cylindrical tubular shape for the distal end of the catheter and the tubular distal tip may also be suitable.

The tubular distal tip is preferably formed of a yieldable material that is sufficiently rigid to retain the proximal end 28 of an endoluminal device within the inner lumen of the tubular distal tip. The yieldable material can be, for example, a shape memory polymer, an elastomer such as polyurethane, nylon, PEBAX polymer, Teloflex, polybutyl terephthalate (PBT), polymers available under the trade names PEBAX, Hytrel, Arnitel, Riteflex, heat shrink tubing such as polyethylene terephthalate (PET) or high density polyethylene (HDPE), or a shape memory metal such as nickel titanium alloy, such as that available under the trade name NITINOL.

The proximal end of the endoluminal therapeutic device preferably has a stem portion 30 with an enlarged proximal end such as a ball 32, coil, block or the like, captured within the inner lumen of the tubular distal tip, and the endoluminal therapeutic device is typically an embolic coil, although the endoluminal therapeutic device can also be a stent, or a similar device to be implanted at a treatment site in the vasculature of a patient.

Figure 2:
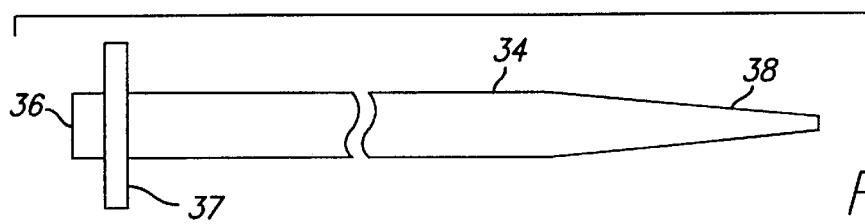
FIG. 2 is a side elevational view of a first embodiment of the pusher member of the endoluminal device delivery assembly of FIG. 1.

Means are also provided for dislodging the proximal end of the endoluminal device captured in the inner lumen of the tubular distal tip to expel the proximal end of the endoluminal device from the distal opening of the tubular distal tip at the desired location for treatment within the vasculature of a patient. As is illustrated in FIGS. 1 and 2, in a presently preferred embodiment the means for dislodging the proximal end of the endoluminal device from the inner lumen of the tubular distal tip comprises an elongated flexible pusher member 34 such as a flexible metal wire coaxially disposed within the elongated flexible tubular catheter. The proximal end 36 of the pusher member extends from the proximal end of the elongated flexible tubular catheter, and preferably includes a stop portion 37 at the proximal end of the pusher member for limiting the movement of the pusher member through the delivery catheter, and the distal end 38 of the pusher member is adapted to contact and dislodge the proximal end of the endoluminal device from the tubular distal tip. As noted above, in one preferred embodiment, the distal end of the elongated flexible tubular catheter is narrowed, and preferably has a frustoconical shape for improved tracking of the endoluminal device delivery assembly, and the distal end of the pusher member has a corresponding frustoconical shape, so as to extendable to the distal end of the catheter to force the proximal end of the endoluminal device from the yieldable tubular distal tip to dislodge the proximal end of the endoluminal device.

Figure 3:
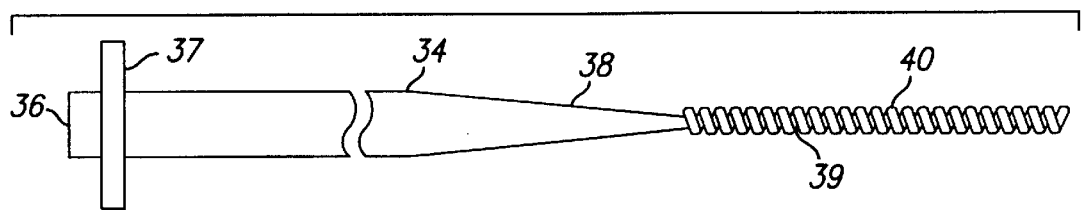
FIG. 3 is a side elevational view of an alternate embodiment of the pusher member of the endoluminal device delivery assembly of the invention.
Figure 4:
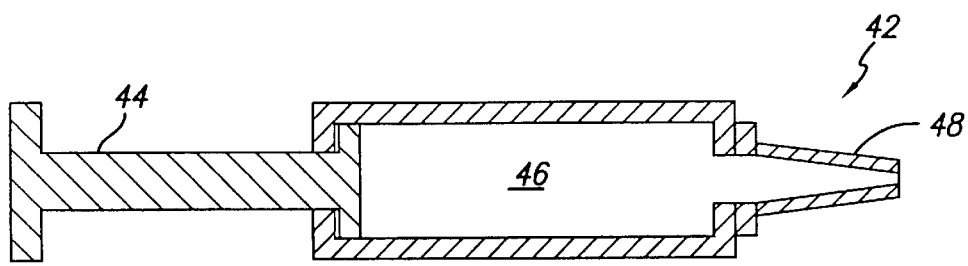
FIG. 4 is a sectional view of a syringe for use in combination with the catheter of the endoluminal device delivery assembly of the invention in another embodiment.

In an alternate preferred embodiment illustrated in FIG. 3, the distal end 38 of the pusher member 34 has a narrowed distal cylindrical tip 39, and a flexible coil 40 is mounted to the distal tip 39 of the elongated pusher member, such as by an adhesive such as cyanoacrylate, or heat bonding, and when the coil is formed of metal, by solder, welding, or the like. The flexible coil contacts the proximal end of the endoluminal device when the pusher member is moved distally through the delivery catheter, and reduces stiffness at the distal end of the pusher member, allowing for improved tracking of the endoluminal device delivery assembly within the vasculature, and can be formed from a shape memory polymer, a nickel titanium alloy, stainless steel, or platinum, for example, or other similar suitable materials.

In another presently preferred embodiment, the tubular distal tip is dimensioned so as to form a tight fluid seal about the proximal end of the endoluminal device, and the means for dislodging the endoluminal device comprises a syringe 42 having a plunger 44 for pressurizing fluid, such as saline, for example, in a fluid chamber 46 to supply pressurized fluid through a nozzle 48 that can be connected to the proximal end of the elongated flexible tubular catheter for supplying the pressurized fluid within the elongated flexible tubular catheter to expel the proximal end of the endoluminal device from the tubular distal tip.

In the method of delivering an endoluminal therapeutic device into the vasculature of a patient, the dislodging element, such as the pusher member, other similar mechanical device, or the pressurized fluid from the syringe, is introduced into the proximal end of the elongated flexible catheter to dislodge the proximal end of the endoluminal device from the tubular distal tip to expel the proximal end of the endoluminal device through the distal opening of the tubular distal tip at the desired location for treatment within the vasculature of a patient. The elongated pusher member thus can be introduced and moved coaxially distally within the elongated flexible tubular catheter to contact and dislodge the proximal end of the endoluminal device from the tubular distal tip. Although in this embodiment a fluid seal need not be formed by the tubular distal tip over the proximal stem portion of the endoluminal device, when the distal tip is dimensioned to form a fluid seal about the proximal end of the endoluminal device, and a syringe or a similar device can be connected to the proximal end of the elongated flexible tubular catheter for supplying pressurized fluid within the elongated flexible tubular catheter to force the yieldable tubular distal tip of the catheter open to expel the proximal end of the endoluminal device from the tubular distal tip, to release the endoluminal device at the desired treatment site.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An endoluminal delivery device for deployment of an endoluminal therapeutic device at a desired location for treatment within the vasculature of a patient, the endoluminal therapeutic device, the endoluminal device delivery comprising:

an elongated flexible tubular catheter having a distal end; and a tubular distal tip having a proximal end mounted to the distal end of said catheter, an inner lumen, and a distal end with a surface defining a distal opening for releasably holding the proximal end of the endoluminal device within the inner lumen of said tubular distal tip, wherein the diameter of the distal end of the tubular distal tip is smaller than the diameter of the proximal end of the tubular distal tip, said tubular distal tip being formed of a yieldable material for releasably retaining an endoluminal therapeutic device.

2. The endoluminal delivery device of claim 1, wherein said yieldable material is selected from the group consisting of a shape memory polymer, a shape memory metal, an elastomer, polyethylene terephthalate and high density polyethylene.

3. The endoluminal delivery device of claim 1, wherein said endoluminal therapeutic device has a stem portion with an enlarged proximal end captured within said inner lumen of said tubular distal tip.

* * * * *

UNITED STATES PATENT AND TRADEMARK OFFICE
CERTIFICATE OF CORRECTION

PATENT NO.   : 6,319,267 B1
DATED        : November 20, 2001
INVENTOR(S)  : Daniel R. Kurz It is certified that error appears in the above-identified patent and that said Letters Patent is hereby corrected as shown below:

<u>Title page,</u>
Item [56], Reference Cited, FOREIGN PATENT DOCUMENTS, add the following
-- WO   00/12015        3/2000         (WO) --.

Signed and Sealed this

Sixth Day of August, 2002

*Attest:*

JAMES E. ROGAN
*Attesting Officer*       *Director of the United States Patent and Trademark Office*